(12) United States Patent
Kim

(10) Patent No.: US 11,432,801 B2
(45) Date of Patent: Sep. 6, 2022

(54) INTERVENTIONAL ULTRASOUND PROBE

(71) Applicant: Duke University, Durham, NC (US)

(72) Inventor: Charles Y. Kim, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 135 days.

(21) Appl. No.: 16/603,028

(22) PCT Filed: Apr. 6, 2018

(86) PCT No.: PCT/US2018/026413
§ 371 (c)(1),
(2) Date: Oct. 4, 2019

(87) PCT Pub. No.: WO2018/187658
PCT Pub. Date: Oct. 11, 2018

(65) Prior Publication Data
US 2020/0069290 A1    Mar. 5, 2020

Related U.S. Application Data

(60) Provisional application No. 62/482,387, filed on Apr. 6, 2017.

(51) Int. Cl.
*A61B 8/14* (2006.01)
*A61B 8/00* (2006.01)
*A61B 8/08* (2006.01)
*A61B 17/34* (2006.01)

(52) U.S. Cl.
CPC .......... *A61B 8/4494* (2013.01); *A61B 8/0841* (2013.01); *A61B 17/3403* (2013.01); *A61B 2017/3413* (2013.01)

(58) Field of Classification Search
CPC combination set(s) only.
See application file for complete search history.

(56) References Cited

U.S. PATENT DOCUMENTS

| | | | |
|---|---|---|---|
| 4,408,611 A | 10/1983 | Enjoji | |
| 4,475,553 A | 10/1984 | Yamaguchi et al. | |
| 4,489,730 A | 12/1984 | Jingu | |
| 4,542,747 A | 9/1985 | Zurinski et al. | |
| 2005/0101868 A1* | 5/2005 | Ridley | A61B 8/4444 600/459 |
| 2007/0016030 A1* | 1/2007 | Stringer | G01S 15/8925 600/437 |

(Continued)

*Primary Examiner* — Joel F Brutus
(74) *Attorney, Agent, or Firm* — Polsinelli PC

(57) ABSTRACT

A method and system are provided for guiding a needle to a target location within a subject. The system comprises a probe and a needle guide. The probe includes two or more transducers that are arranged to direct sound waves toward a target location on a subject. The needle guide can be detachably coupled to the probe, and may be used to maintain the needle within viewing planes of the transducers while the needle is inserted into the subject. To facilitate guidance of the needle, a real-time image of the target region can be produced by overlaying images produced by the two or more transducers. Such a system may provide a more adaptive and reliable way to guide the insertion of a needle, allowing for more sophisticated and fool-proof viewing planes, improved versatility, and more ergonomic needle control.

14 Claims, 5 Drawing Sheets

(56) References Cited

U.S. PATENT DOCUMENTS

| | | |
|---|---|---|
| 2007/0208255 A1 | 9/2007 | Ridley et al. |
| 2010/0298702 A1 | 11/2010 | Rogers et al. |
| 2011/0301451 A1 | 12/2011 | Rohling |
| 2012/0057428 A1* | 3/2012 | Specht ................ A61B 8/4254 367/13 |
| 2014/0257110 A1 | 9/2014 | Chang et al. |
| 2016/0374644 A1* | 12/2016 | Mauldin, Jr ......... A61B 8/5223 600/424 |

* cited by examiner

INTERVENTIONAL ULTRASOUND PROBE

CROSS-REFERENCE TO RELATED APPLICATION

The present application is a national stage entry of PCT/US18/26413 filed Apr. 6, 2018, which claims priority to U.S. Provisional Application No. 62/482,387 filed Apr. 6, 2017, the contents of which are hereby incorporated by reference.

BACKGROUND

Unless otherwise indicated herein, the materials described in this section are not prior art to the claims in this application and are not admitted to be prior art by inclusion in this section.

Insertion of needles into blood vessels is a common intervention for insertion of venous catheters, arterial catheters, and blood sampling. Similarly, insertion of biopsy needles into tumors and other tissues can provide diagnostic information to guide treatment. Use of real-time ultrasound can greatly improve accuracy of these tasks by allowing visualization of the needle entering the target structure. Additionally, the use of ultrasound guidance can reduce complications and improve speed by allowing visualization of the non-target organs and structures surrounding the target structure. Given these benefits, ultrasound is routinely utilized for insertion of venous catheters and biopsy of lesions in solid organs. Despite its widespread use, ultrasound guidance is frequently performed suboptimally, because optimal use of ultrasound for needle guidance is a challenging skill that benefits from specialized training and substantial experience to establish proficiency. Specifically, maintaining the needle within the viewing plane of the ultrasound beam is important for proper visualization of the needle path. However, such a task is highly challenging.

Needle guides exist for the purpose of maintaining the needle along a viewing plane of the ultrasound. Such needle guides may include clip-on attachments for ultrasound transducers that help guide the angle and trajectory of a needle. However, due to conventional needle guides being positioned at a peripheral aspect of the ultrasound transducer, the needle angle increases the distance to be traversed to the target region. Furthermore, existing guide systems provide that the needle traverse various tissue layers at an angle, which can skew the needle path. This skewing can potentially cause the needle to leave the viewing plane of a given transducer and render the ultrasound guidance technique ineffective.

SUMMARY

The present disclosure generally relates to a system and method for an interventional ultrasound probe that provides guidance for a needle inserted into a subject. Such a system may include two or more transducers and a needle guide that positions a needle within the viewing planes of the transducers, allowing the needle to be visualized in real-time by a user.

In a first aspect, a system is provided. The system includes a probe and a needle guide detachably coupled to the probe. The probe comprises a first transducer and a second transducer. The first transducer and second transducer are arranged such that sound waves provided by the first and second transducers are emitted toward a target location of a subject. The needle guide is disposed between the first transducer and the second transducer such that a needle inserted through the needle guide is configured to extend toward the target location.

In a second implementation, a method is provided. The method includes positioning a first transducer and a second transducer proximate to a target location of a subject. The needle guide is disposed between the first transducer and the second transducer such that a needle inserted through the needle guide is configured to extend toward the target location. The method further includes causing the first transducer and the second transducer to emit sound waves such that at least a portion of the sound waves are emitted toward the target location. Additionally, the method includes receiving, at the first and second transducers, information indicative of reflected sound waves and generating a real-time image of the target location based on the received information. Yet further, the method includes inserting a needle through the needle guide so as to intersect with the target location.

Other aspects, embodiments, and implementations will become apparent by reading the following detailed description with reference, where appropriate, to the accompanying drawings.

DETAILED DESCRIPTION

Figure 1A:
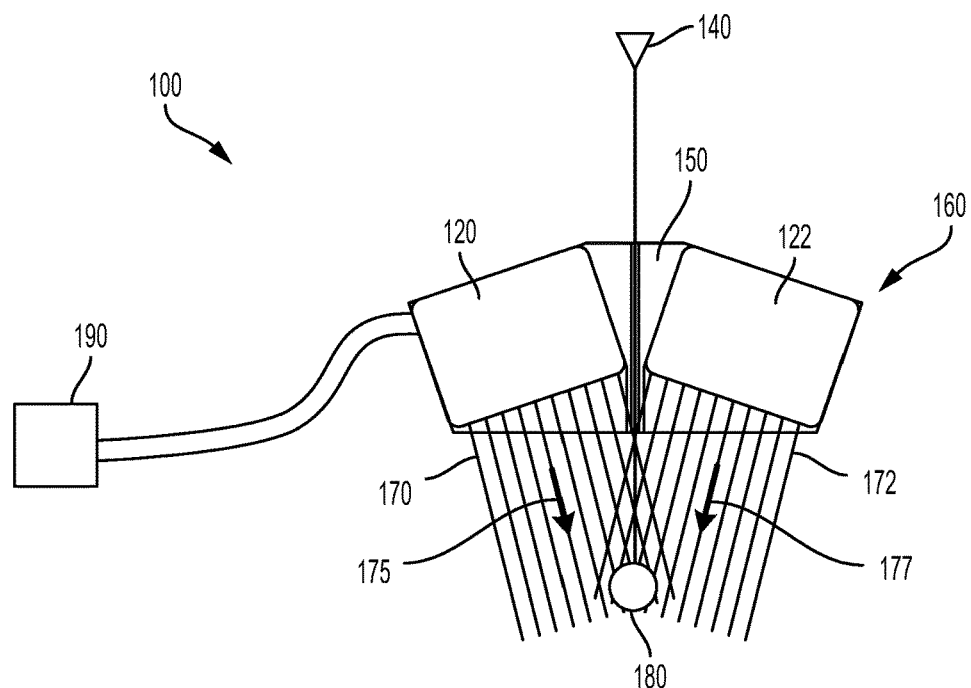
FIG. 1A illustrates a side view of a probe, according to an example embodiment.

Example methods, devices, and systems are presently disclosed. It should be understood that the word "example" is used in the present disclosure to mean "serving as an instance or illustration." Any implementation or feature presently disclosed as being an "example" is not necessarily to be construed as preferred or advantageous over other implementations or features. Other implementations can be utilized, and other changes can be made, without departing from the scope of the subject matter presented in the present disclosure.

Thus, the example implementations presently disclosed are not meant to be limiting. Components presently disclosed and illustrated in the figures can be arranged, substituted, combined, separated, and designed in a wide variety of different configurations without departing from the scope of this disclosure.

Unless context suggests otherwise, the features illustrated in each of the figures can be used in combination with one another. Thus, the figures should be generally viewed as components of one or more overall implementations, with the understanding that not all illustrated features are necessary for each implementation.

In an effort to provide technical context for the present disclosure, the information in this section can broadly describe various components of the implementations presently disclosed. However, such information is provided solely for the benefit of the reader and, as such, does not expressly limit the claimed subject matter. Further, components shown in the figures are shown for illustrative purposes only. As such, the illustrations are not to be construed as limiting. As is understood, components can be added, removed, or rearranged without departing from the scope of this disclosure.

Further, while embodiments disclosed herein may make reference to use on or in conjunction with a living human body, it is contemplated that the disclosed methods, systems, and devices may be used in any environment where guided needle insertion is desirable. The term "subject" may refer to any living or non-living body or a portion thereof. In some embodiments, the subject is a human patient.

Additionally, the term "target location" as used herein should be understood broadly to include any internal or external region, feature, tissue, organ, lesion, vessel, area of skin, cavity, tumor, lumen, or any other desired target for a guided needle.

I. Overview

For particular applications, it could be beneficial to provide a system and method for guiding a needle to a target location on a subject. For instance, a medical professional may desire to guide a needle into a blood vessel for insertion of venous catheters, arterial catheters, or blood sampling. Likewise, guidance of needles into other tissues may be important for biopsies, diagnostic testing, amniocentesis, thermal ablation, fluid drainage, and other procedures. In such cases, it can be advantageous to use a needle guidance system that provides real-time ultrasound imaging of the target location. By generating a real-time image of a target location using two or more ultrasound transducers, a user may be able to visualize a needle throughout its entire path from skin to target. A needle guidance system may also desirably include a wide ultrasound viewing plane (i.e. sonographic plane). For many procedures, it could also be advantageous to constrain the path of the needle along the center of the sonographic plane of the transducers using e.g., a needle guide, in order to reduce error. Furthermore, perpendicular insertion of the needle may also be desirable, limiting the needle's parenchymal path to reach a target location.

Systems, devices, and methods herein generally relate to controllably guiding a needle to a target location. Specifically, needle guidance may be carried out using a system including a probe (e.g., an interventional ultrasound probe) and a needle guide.

The probe may include a plurality of transducers operable to visualize a needle in real-time using ultrasound or another imaging technique. Providing two or more transducers arranged proximate to the intervention site may improve visualization of the target location and/or needle, broaden the viewing plane, and reduce the risk of "losing" the needle in a "blind spot" at an edge of the transducer's viewing plane. Images from the plurality of transducers can be geometrically overlaid to enhance the user's view of the target region and/or the needle and reduce the chance of error in interventional procedures.

In an example, the probe may include a first transducer and a second transducer arranged such that sound waves provided by the first and second transducers are emitted toward a target location of a subject. The transducers could be arranged in the same plane relative to the target location and angled toward each other such that their respective sound waves converge at the target location. In some embodiments, the number, type, size, and arrangement of the transducers may vary depending on the environment of use, the nature of the medical intervention, and the target tissue. For instance, in some examples, a probe could include three, four, five, six, or more transducers arranged to image the target location. Similarly, the transducers could be arranged such that sound waves are directed to propagate through opposite sides of the target location (i.e., to approximate a "front" and "back" view), in parallel directions, in perpendicular directions, or from a range of different angles surrounding the target location.

Likewise, the probe may come in a range of shapes and sizes. For instance, a probe configured for external use (e.g., on a subject's skin) could include a diameter in a range of about 2 cm to 10 cm. Alternatively, a smaller form factor may be desired for internal use, with a diameter ranging from about 5 mm to 20 mm for internal applications. In yet a further example, the probe may be sized for endovascular use within arteries or veins, and may have a still smaller form factor (e.g., 5 mm diameter or less).

The system may also include a needle guide detachably coupled to the probe between the two transducers, such that a needle inserted through the needle guide is configured to extend toward the target location. For example, the needle guide could be disposed in between two or more of the transducers, in a space within a housing of the probe, or in another location that facilitates needle entry through the guide and into the subject along the ultrasound imaging plane. The needle guide could be configured to constrain a needle along a specified path in the direction of the target location (e.g., a path along a center of a sonographic plane of the transducers). In some examples, the needle guide may be disposable and provided separately from the probe. In such cases, the needle guide may include a coupler (e.g., a shaft coupling, a magnetic coupling, a clip coupling, a mating coupling, or another coupling mechanism) so that the needle guide can be secured to the probe prior to and during needle guidance and can be removed and replaced after use.

Further, such a system could include a controller communicatively coupled to the transducers. The controller may be configured to actuate the transducers to emit sound waves, receive information at the transducers indicative of reflected sound waves, and/or generate a real-time image of the target location to guide insertion of the needle. A real-time image of the target location may be created by generating a first and second image of the target location based on information received from the first and second transducers, respectively, and superimposing (i.e., overlaying) or merging the respective images to provide a real-time 3-dimensional composite image. The controller could further be communicatively coupled to a display (e.g., an ultrasound monitor). Images produced by each transducer could be viewed as separate real-time images on the display. In some embodiments, the controller may also allow a user to affect operation of the transducers, e.g., by changing an ultrasound emission frequency (or frequency band) or adjusting a direction of propagation of the emitted sound waves.

II. Example System

FIG. 1A illustrates a side view of a system 100 according to an example embodiment of the present disclosure. As shown in FIG. 1A, one aspect of system 100 includes a probe 160 and a needle guide 150 detachably coupled to the probe 160. The probe 160 includes a first transducer 120 and a second transducer 122. Sound waves 170 provided by the first transducer 120 propagate along a first propagation direction 175, and sound waves 172 provided by the second transducer propagate along a second propagation direction 177. The first transducer 120 and the second transducer 122 may be arranged such that the sound waves 170 and 172 provided by the first transducer 120 and second transducer 122 are emitted toward a target location 180 on a subject. That is, the first transducer 120 and the second transducer 122 may be arranged at an angle with respect to each other such that the sound waves 170 and 172 transmitted therefrom create overlapping viewing planes (i.e., an image regions that are visible by the first transducer 120 and/or second transducer 172) over the target location 180.

Figure 1B:
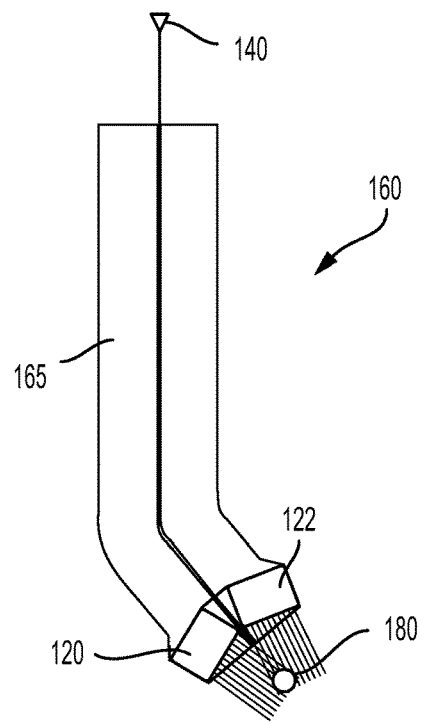
FIG. 1B illustrates a side view of an endocavitary probe, according to an example embodiment.

The system 100 of the present disclosure may be configured to guide the needle 140 to a range of structures, for instance, a tissue, vessel, tumor, organ, lesion, area of skin, lumen, or body cavity. In some cases, the system 100 could be configured for external use, and the probe 160 could be configured to be positioned over a skin area of the subject. Additionally or alternatively, in some embodiments the system 100 could be configured for internal use (e.g., use within a body cavity, for instance, the gastrointestinal tract, bronchial tree, rectum, vagina, urethra, ureter, biliary tree, peritoneal cavity, or pleural cavity). FIG. 1B illustrates such an embodiment, where the first transducer 120 and the second transducer 122 are arranged within a probe 160 configured for internal use. In some embodiments, probe 160 could be termed an endoscopic probe, an endocavity probe, or an endocavitary probe without limitation. Such a probe 160 could include a smaller form factor, with a diameter ranging from about 5 mm to 20 mm. For endovascular use (i.e., within arteries or veins), the probe 160 could include a still smaller form factor, for example, 5 mm diameter or less. In some examples, the probe 160 could include a shaft 165 that is articulated such that the probe can bend and conform to its environment (e.g., the shape of a tract, body cavity, or vasculature). In some embodiments, a directionality and/or articulation of the probe 160 could be controllable by e.g., a controller in communication with the probe 160. Controllable articulation and/or directionality may facilitate operation of the probe 160 by allowing more precise navigation of body cavities and/or multidirectional imaging and needle insertion.

Returning to FIG. 1A, the first transducer 120 and the second transducer 122 may be configured to emit sound waves 170 and 172 toward a target location 180 and receive information indicative of reflected sound waves from the target location 180. The transducers 120, 122 may provide sound waves 170 and 172 at a range of different and/or adjustable frequencies or frequency ranges. For instance, sound waves 170 and 172 provided by the first transducer 120 and the second transducer 122 may vary depending on a depth of the target location 180 (i.e., a distance from a skin surface or another lumen of the subject), a distance of the target location 180 from the probe 160, a size or shape of the target location or feature, a tissue density or characteristic, or another variable. In some example embodiments, the sound waves 170 and 172 provided by the first transducer 120 and the second transducer 122 could include one or more frequencies within a frequency range of about 1 MHz to 22 MHz. Additionally or alternatively, the first transducer 120 and/or the second transducer 122 could include a transducer that operates at lower or higher frequencies. As an example, the emitted sound waves 170 and 172 could include frequencies within a range of about 2 MHz to 7.5 MHz. Many other frequencies or ranges of frequencies may be possible within the scope of the present disclosure. Yet further, in some embodiments, the first transducer 120 and/or the second transducer 122 could include one or more phased array transducers, which could be configured to controllably steer the ultrasonic waves in a desired direction.

In some embodiments described herein, a needle could be guided to a target location based on ultrasound images obtained from information provided by transducers 120, 122. However, the probe 160 may additionally or alternatively be used for photoacoustic imaging, where detection is done by measuring absorption of electromagnetic waves and localized thermal excitation. Other interventional imaging modalities are contemplated.

As used herein, the terms "transducer" and "transducer element" are used interchangeably and refer to the component of the probe 160 that is configured to produce a signal (e.g., sound waves 170 and 172) and receive a further signal (e.g., reflected sound waves) from the target location 180. Transducers 120, 122 may come in a range of shapes, sizes, and configurations as desired for a specific application or treatment area. In some embodiments, a single ultrasound transducer may contain a plurality of elements (e.g., piezoresistive crystals) operable to produce ultrasonic waves. The number or configuration of elements of the transducers 120, 122 may determine the size, shape, and/or resolution of the viewing plane (i.e., image region) of the transducers. For instance, the elements of transducers 120, 122 may be arranged in a rectangular array, in a linear row, in a circular shape, or in any other desired footprint or shape.

Additionally, elements of the first transducer 120 and the second transducer 122 can be arranged to give the transducers a variety of beam shapes, i.e., the direction of propagation 175, 177 of sound waves 170 and 172 produced by the transducers 120, 122. For instance, at least one of the first transducer 120 and/or the second transducer 122 may include elements arranged in a convex shape, such that sound waves 170 and 172 emitted from the transducer propagate radially outward from the given source transducer. Alternatively, at least one of the first transducer 120 and/or the second transducer 122 may include elements arranged in a planar shape (i.e., such that sound waves 170 and 172 propagate along a substantially planar or linear beam path), or a concave shape (i.e., such that sound waves 170 and 172 propagate radially inward toward a target location 180).

In some embodiments, the first transducer 120 and the second transducer 122 could be communicatively coupled (e.g., via a wired or wireless communication interface) to a controller 190. The controller 190 could include, as an example, a computing device configured to control some or all of the operations of the first transducer 120 and the second transducer 122. In example embodiments, the controller 190 could provide electrical signals to the transducers that are transduced or otherwise converted into sound waves (e.g., sound waves 170 and 172). Furthermore, controller 190 could be configured to receive information from the transducers indicative of interactions between the sound waves and a particular environment or location (e.g., a patient's body). The controller 190 could also be configured to form respective ultrasound images based on the received information. The controller 190 could additionally be configured to perform image processing operations (e.g., image merging, image addition, image subtraction, etc.) with the respective ultrasound images so as to provide a merged ultrasound image. In some embodiments, the controller 190 could be similar or identical to controllers 290 and 390 as illustrated and described in reference to FIGS. 2A and 3, respectively.

Figure 2A:
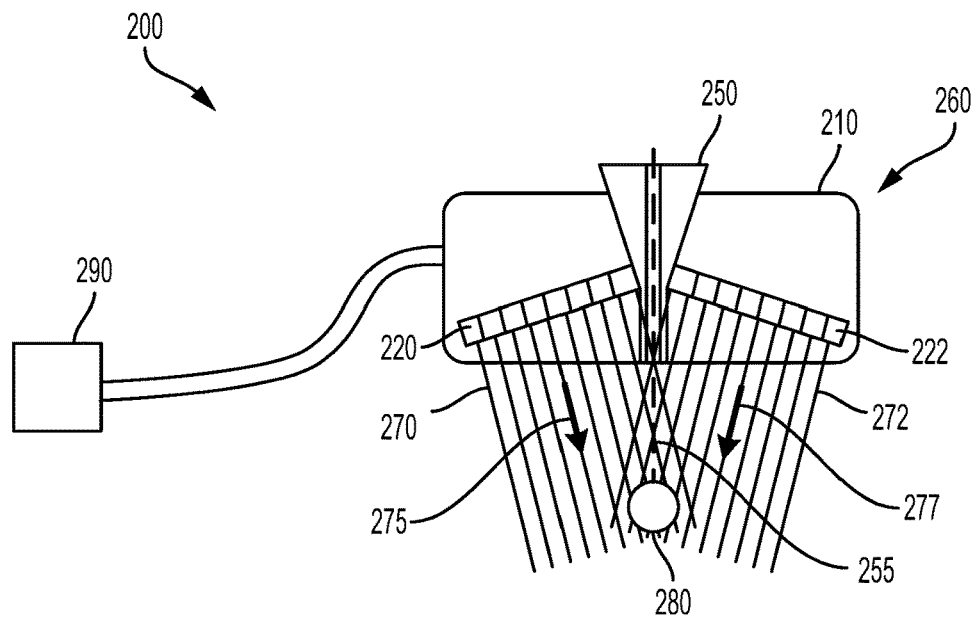
FIG. 2A illustrates a cross sectional side view of a probe that includes linear transducers, according to an example embodiment.

The first and/or second transducers 120, 122 described herein could include any transducer configurations currently known and/or commercially available, such as linear array transducers, convex transducers, phased array transducers, endocavity transducers, pencil transducers, or other types. As illustrated in FIG. 2A, at least one of the first transducer 220 or the second transducer 222 could include a linear array transducer. In such embodiments, transducers 220, 222 could include an array of elements arranged in a generally rectangular or linear arrangement. Adjacent elements may be oriented in substantially the same direction, such that sound waves 270 and 272 emitted from the transducers 220, 222 propagate with a linear beam shape (i.e., along respective parallel paths in the same direction toward the target location 180). However, any transducer type, element configuration, and/or beam shape may be used without departing from the present disclosure.

Figure 2B:
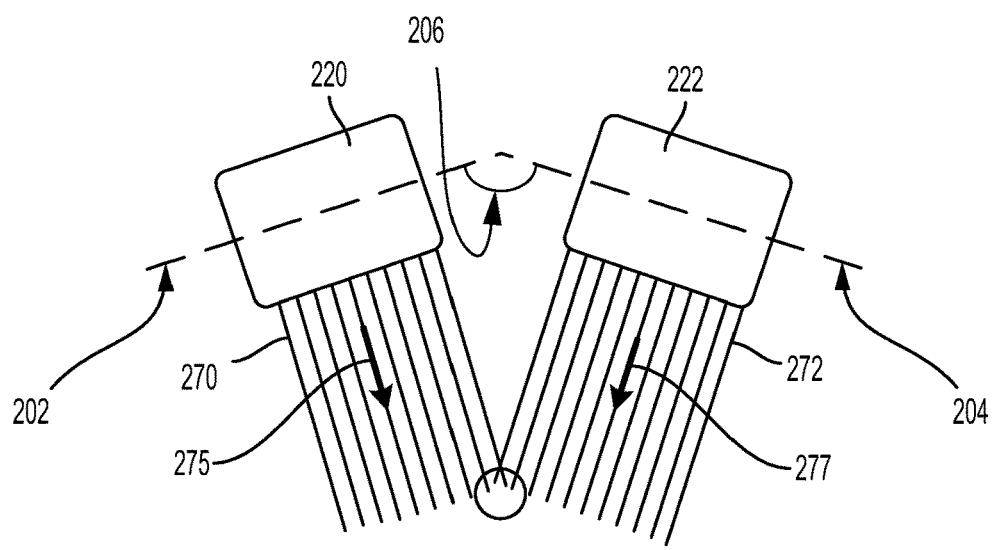
FIG. 2B illustrates a schematic of a transducer arrangement, according to an example embodiment.

The region traversed by the sound waves 270 and 272 emitted from first transducer 220 and the second transducer 222 and reflected from the target location 280 may approximate a viewing plane of the transducers 220, 222. As illustrated in FIG. 2B, sound waves 270 provided by the first transducer 220 may propagate along a first propagation direction 275, while sound waves 272 provided by the second transducer 222 propagate along a second propagation direction 277. The arrangement of the transducers 220, 222 can be selected to optimize the propagation paths of the two transducers, enhance needle visualization, adjust the visible region, improve image resolution, optimize the size or shape of the probe 260, improve placement of needle guide 250, or provide some other benefit. The first transducer 220 and the second transducer 222 may be arranged such that a plane of the first transducer 202 is at a relative angle 206 relative to a plane of the second transducer 204. The relative angle 206 between the transducers 220, 222 could be selected in order to adjust the imaging depth of the probe 260 (i.e., to visualize a needle 240 and/or target area 280 that is farther from the probe 260). In some embodiments, the relative angle 206 could be selected from values within a range of about 90 degrees to 170 degrees. In other embodiments, the relative angle 206 may be adjustable, such that sound waves 270 and 272 provided by the first transducer 220 and the second transducer 222 are controllably emitted toward a selectable target location 280.

As illustrated in FIG. 2A, the transducers 220, 222 may be positioned on opposite sides of the needle guide 250. In such a configuration, sound waves 270 and 272 emitted from the first transducer 220 and the second transducer 222 are directed toward opposite sides of a needle when a needle is inserted through the needle guide 250 and extended toward the target location 280, thereby providing a "front" and "back" view of the target location 280. However, the first transducer 220 and the second transducer 222 may be arranged such that the sound waves 270 and 272 emitted therefrom intersect at a variety of angles relative to the target location 280. In another example, the first transducer 220 and the second transducer 222 are arranged to provide a "front" and "side" view, respectively, when the needle is extended into the target location 280. In such an example, the first transducer 220 may be offset approximately 90 degrees from the second transducer 222 relative to the needle guide 250 and/or target location 280. In this configuration, sound waves 270 and 272 emitted from the first transducer 220 and the second transducer 222 may converge at the target location 280, where the first propagation direction 275 and the second propagation direction 277 are substantially perpendicular.

In some examples, the propagation direction of the first transducer 220 and/or the second transducer 222 could be adjustable (i.e., by adjusting a plane of the first transducer 202 or a plane of the second transducer 204) so as to allow a user of the probe 260 to adjust a field of view and/or a depth of field of the area that is imaged. For instance, it could be desirable to change an angle of one or more of the transducers 220, 222 relative to the target location 180 to visualize a feature that is farther away from the probe 260, or to follow a needle as it is inserted further into the subject. In such an example, the first propagation direction 275 and the second propagation direction 277 may be selected (e.g., through a controller 290 or a user interface of the probe 260), such that sound waves 270 and 272 provided by the first transducer 220 and the second transducer 222 are controllably emitted toward a selectable or desired target location 280.

The first transducer 220 and second transducer 222 may be secured within the probe 260 in any suitable manner that maintains the transducers 220, 222 in their correct position, such as fasteners, epoxies, glues and the like. Additionally or alternatively, the transducers 220, 222 may be secured within the probe 260 by way of a housing 210, a scaffolding, etc. Such a housing 210 may be configured to surround the first transducer 220 and the second transducer 222 and/or provide mechanical support for the needle guide 250. In some embodiments, the first transducer 220 and/or the second transducer 222 are removable from the housing 210 such that the transducers 220, 222 can be rearranged, replaced, and/or repaired. However, in other examples, the transducers 220, 222 could be permanently affixed to the housing 210 and/or scaffolding of the probe 260.

In some cases, the housing 210 of the probe 260 includes a space positioned between the first transducer 220 and second transducer 222 (i.e., a space shaped to receive a needle guide 250). The space may be of such a size and configuration so as to accommodate a disposable needle guide 250 such that a needle inserted through the needle guide 250 will pass through the overlapping viewing planes generated by the transducers 220, 222 and intersect the target location 280. The space may be located such that a needle inserted through the needle guide 250 is configured to extend toward the subject in a direction substantially perpendicular to a skin surface or other surface of the subject. In some embodiments, the space in the housing 210 may also include a coupler (e.g., a shaft coupling, a magnetic coupling, a clip coupling, or a mating coupling) or some other attachment mechanism configured to secure the needle guide 240 to the probe 260.

The system 200 may further include a needle guide 250 for directing the path of a needle into the target location 280 (e.g., into a portion of a subject that is within the viewing plane of the transducers 220, 222). As shown in FIG. 2A, the needle guide 250 may be disposed between the first transducer 220 and second transducer 222 such that a needle inserted through the needle guide 250 is configured to extend toward the target location 280. In order to be visualized by the transducers 220, 222, the path of the needle must intersect the sound waves 270 and 272 such that the sound waves may be reflected from the needle and returned to the transducers 220, 222. Accordingly, the needle guide 250 may be disposed such that a path of the needle is angled to intersect the direction of propagation 275, 277 of at least one of the first transducer 220 and/or the second transducer 222 (i.e., such that the needle does not run parallel to the direction of propagation of the sound waves 270 and 272). In other words, in some embodiments the needle guide 250 constrains the needle in a specified path 255, which may extend toward the target location 280 through the viewing planes of the transducers. As described herein, the specified path 255 may be substantially perpendicular to a skin surface or other surface of the subject. In other embodiments, the specified path 255 may be oriented such that a needle is inserted at a specified angle relative to the skin, relative to the probe 260, or in some other specified path. Yet further, in some examples the needle and/or needle guide 250 may be manipulable such that a user of the probe 260 may manipulate the needle as necessary to reach the target location 280.

In some examples, the needle guide 250 may be supplied separately from the probe 260 so that it may be provided in a sterile state and disposed of after use (e.g., after a single use, after use on a single patient or by a single practitioner, or after another pattern of use). In such a case, the needle guide 250 may be detachably coupled to the probe 260, such that a user may secure the needle guide 250 prior to and during insertion of the needle, and then remove and replace the needle guide 250 after use. The needle guide 250 may be formed of any number of suitable materials, such as plastics and/or polymers; however, other materials such as metal, ceramics, and/or composite materials may be used.

In some examples, the needle guide 250 includes a coupler configured to secure the needle guide to the probe 260. The coupler could be configured to detachably couple the needle guide 250 to the probe 260, to a housing 210 of the probe 260, to a space in the probe 260 and/or housing 210, or at some other element of the system 200. In various embodiments, the coupler could include a shaft coupling, a magnetic coupling, a clip coupling, or a mating coupling; however, other types of couplings are contemplated.

To facilitate operation of the probe 260, the system 200 may further include a controller 290 communicatively coupled to the first transducer 220 and the second transducer 222. As defined herein, the term "communicatively coupled" includes both hardwiring, such as by a cable, or wireless communication. In some examples, the controller 290 communicates with the first transducer 220 and the second transducer 222 via a wireless communication protocol. Wireless communication protocols include, but are not limited to, BLUETOOTH®, Wi-Fi, IRdA®, ZIGBEE®, WiMAX®, wireless infra-red, and wireless USB. The controller 290 may also communicate with the transducers 220, 222 over a wireless network, which could include, but need not be limited to, mobile body area networks (MBAN), CDPD, CDMA, GSM, PDC, PHS, TDMA, FLEX, ReFLEX, iDEN, TETRA, DECT, DataTAC, Mobitex, EDGE, 2G, 3G, 4G, and LTE.

While some examples and figures herein describe devices or systems that include some elements (e.g., transducers) as being physically coupled in a wired fashion to other elements of the system (e.g., a controller), it will be understood that embodiments including wireless communication between at least two device or system elements are also contemplated. As an example, some embodiments could include a transducer and needle guide portion that is wirelessly coupled to a corresponding controller. Such wireless coupling could provide several benefits. For example, a medical profession might be able to more easily manipulate the sensor or probe portion without the wired connection. Additionally or alternatively, a probe diameter of a probe (e.g., an endoscopic probe, an endocavity probe, or an endocavitary probe) could be smaller due to no need for a physical wire connection between the transducers and their corresponding controller.

In some examples, the controller 290 is an image processing unit of an ultrasound system, and includes additional software to allow for image overlay/merging and multi-plane viewing. The controller 290 may include a processor and a memory and be operable to execute operations of the system 100. For example, the controller 290 may be operable to actuate the first transducer 220 and/or second transducer 222 to emit sound waves 270 and 272 toward a target location 280 and receive information indicative of reflected sound waves from the location. In some examples, the controller 290 is configured to store the data (i.e., the received information) and/or transmit the data to corresponding computing devices, such as an associated computer, a mobile device, or a cloud network server.

The controller 290 may also be configured to aid in the processing of information (i.e., raw data) received from the first transducer 220 and second transducer 222. For example, the controller 290 could be operable to generate a real-time 3-dimensional image of the target location 280 based on the received information to visualize the insertion of a needle and/or guide the needle to the target location 280. More specifically, the controller 290 could be operable to generate a first image of the target location 280 based on information received by the first transducer 220. The controller 290 could additionally be operable to generate a second image of the target location 280 based on information received by the second transducer 222. The controller 290 may also be operable to overlay the first image and the second image to provide a real-time and/or 3-dimensional image of the needle and/or target location 280. In some embodiments, the controller 290, the first transducer 220, and/or the second transducer 222 could be communicatively coupled to a display (e.g., an ultrasound monitor). In such an embodiment, the controller 290 could be operable to display the first image, the second image, and/or the real-time 3-dimensional rendering of the target location based on the first and second images.

The controller 290 could also be configured to adjust various aspects of the operation of the transducers 220, 222. For example, the controller could be configured to adjust a frequency of sound waves 270 and 272 emitted by at least one of the first transducer 220 or the second transducer 222. The controller may also be configured to adjust a direction of propagation of sound waves 270 and 272 emitted from the transducers 220, 222, i.e., to adjust a viewing plane (i.e., image region) of the system. Additional or alternative functions of the controller 290 are contemplated herein.

Figure 3:
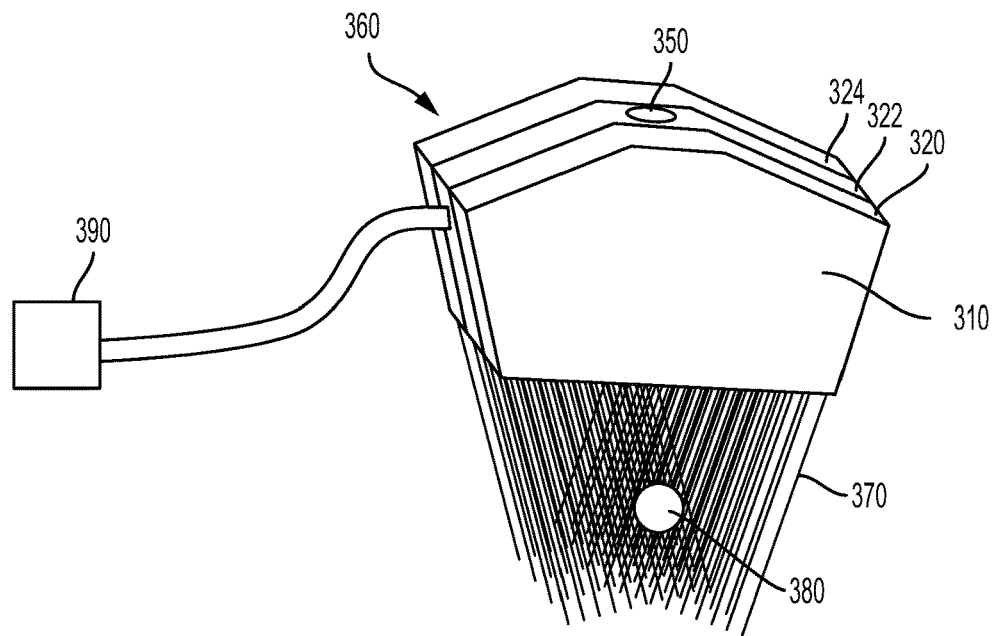
FIG. 3 illustrates a perspective view of a probe, according to an example embodiment
Figure 4:
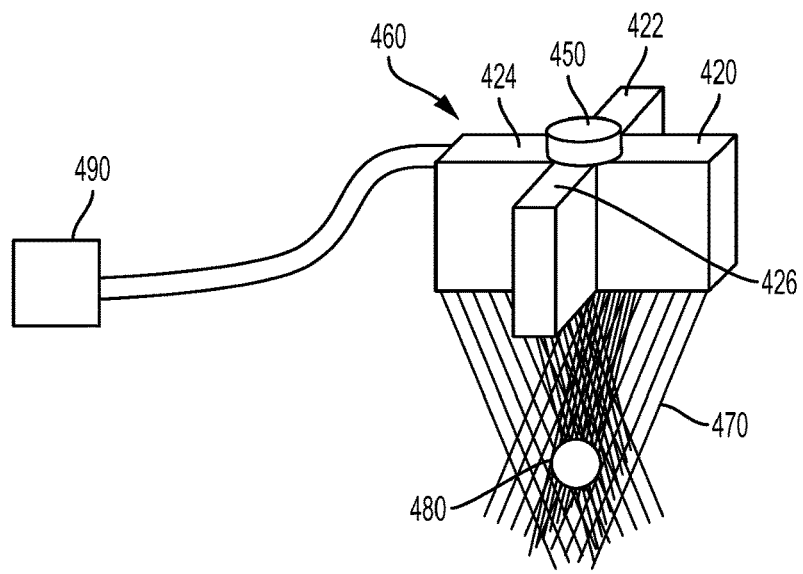
FIG. 4 illustrates a perspective view of a probe, according to an example embodiment

While systems 100, 200 have insofar been described as including a first and second transducer, an interventional ultrasound probe according to the present disclosure may comprise other configurations. As illustrated in FIGS. 3-4, in some embodiments the probe 360 may include a third transducer 324 or even further transducers to aid in visualization of the needle and/or the target location. In some embodiments, a third transducer 324 may be arranged such that sound waves 370 provided by the third transducer 324 are emitted toward the target location 380 (i.e. such that a viewing plane of the third transducer 324 converges with the target location). The third transducer 324 or a further transducer may also be communicatively coupled to a controller 390 such that information received from the transducer can be processed and/or used for generation of a real-time image. In such embodiments, the controller 390 could be communicatively coupled to a display, and real-time images generated from each transducer could be displayed separately. Additionally or alternatively, images from some or all of the transducers could be merged to provide a real-time 3-dimensional image, using e.g., an image processing software to render the image.

A first transducer 320, a second transducer 322, and third transducer 324 of a probe 360 may be arranged in a number of configurations relative to a target location 380 to be imaged. FIG. 3 illustrates one such configuration, including a first transducer 320, a second transducer 322, and a third transducer 324 coupled according to an arrangement. In some examples, the arrangement could include a concave shape, such that sound waves 370 propagated from the transducers 320, 322, 324 converge on the same target location 380. As shown in FIG. 3, at least one of the first transducer 320, the second transducer 322, and/or the third transducer 324 could include one or more linear array transducers. In some examples, a plurality of linear array transducers may be arranged in parallel planes such that sound waves 370 emitted from the plurality of transducers form a plurality of viewing planes that converge at the target location 380. In such an arrangement, the direction of propagation of sound waves 370 emitted from the first transducer 320, the second transducer 322, and the third transducer 324 may be substantially parallel, such that a plurality of approximately parallel images may be generated.

As illustrated in FIG. 3, in some examples the first transducer 320, the second transducer 322, and the third transducer 324 could include respective pairs of transducers (i.e., the first transducer 320 includes a first transducer pair, the second transducer 322 includes a second transducer pair, and the third transducer 324 includes a third transducer pair). The plurality of transducer pairs 320, 322, 324 could be arranged in parallel, such that each respective transducer pair is a fixed distance away from an adjacent transducer pair. Parallel transducers pairs 320, 322, 324 could be spaced at any distance away from an adjacent transducer pair, such as approximately 2 mm to 20 mm apart. The respective transducer pairs 320, 322, 324 could be arranged such that sound waves emitted from the respective pairs 320, 322, 324 follow parallel paths, thereby creating an expanded ultrasound image region. Such a spacing could allow visualization of a larger field of view, which may aid in visualization of the needle and/or the target location, particularly if the needle veers could of its specified path. A needle guide 350 may be disposed between two or more of the plurality of transducers 320, 322, 324 (or transducer pairs) such that a needle inserted through the needle guide 350 is configured to extend toward the target location 380. In one example, as illustrated in FIG. 3, the needle guide could be disposed between a central transducer pair 322, such that the needle following a specified path at approximately the center of a viewing plane provided by the transducers 320, 322, 324. A housing 310 may further be provided to provide mechanical support for the arrangement of transducers 320, 322, 324 and/or provide a space for the coupling of a needle guide 350.

Other transducer configurations are also contemplated. As shown in FIG. 4, another aspect of the present disclosure provides a probe 460 including a plurality of linear array transducers 420, 422, 424, 426 that are arranged in a cross-type configuration. Transducers 420, 422, 424, 426 may be positioned in an arrangement such that sound waves 470 emitted therefrom create perpendicular viewing planes over a target location 480. In such an embodiment, a needle guide 450 may be disposed between the plurality of transducers 420, 422, 424, 426. The needle guide 450 may be positioned in such a way that when a needle is inserted through the guide it will pass through the overlapping sound waves produced by the plurality of transducers 420, 422, 424, 426 and extend toward the target location 480. In such an example, the propagation direction of sound waves 470 from one transducer pairing 420, 424 may be perpendicular to the propagation direction of sound waves from a further transducer pairing 422, 426. Such a configuration may allow for more accurate visualization of the needle in two dimensions instead of one.

In yet other embodiments, a probe could comprise a plurality of transducers arranged in a radial fashion, such that sound waves emitted from the transducers propagate at multiple angles relative to the target location. In a particular example, a probe could comprise a first transducer, a second transducer, and a third transducer arranged about a central axis. However, other configurations may employ four, five, six, or more transducers arranged about the same central axis. A needle guide may be configured such that a needle inserted into the needle guide extends along the central axis and toward the target location. Such a configuration may allow for better imaging of the needle if it becomes skewed with respect to a linear path (i.e., a path following the central axis).

While a number of example embodiments have been provided, it is further understood that changes, substitutions, adaptations, etc. may be made in the particular embodiments as described herein while remaining within the scope of the present disclosure.

III. Example Methods

Figure 5:
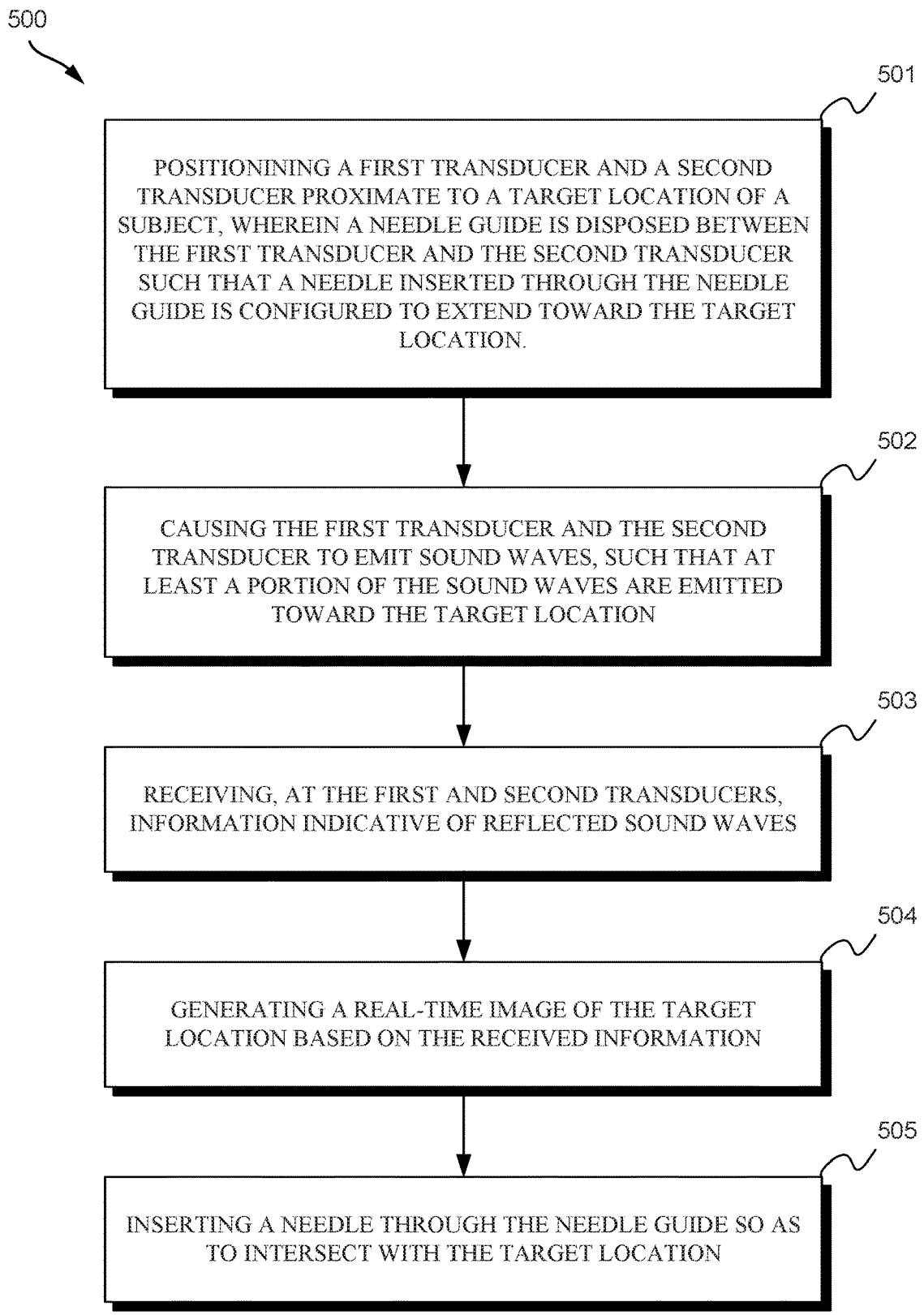
FIG. 5 is a flowchart illustrating a method, according to an example embodiment.

FIG. 5 is a flowchart of a method 500 for guiding a needle to a target location using a system (e.g., an interventional ultrasound probe system) such as any of the systems shown in FIGS. 1A, 1B, 2A, 2B, 3, and 4 and described herein. For purposes of illustration, the system operated in method 500 includes at least a first transducer, a second transducer, and a needle guide. Block 501 of method 500 includes positioning a first transducer and a second transducer proximate to a target location of a subject, wherein a needle guide is disposed between the first transducer and the second transducer such that a needle inserted through the needle guide is configured to extend toward the target location.

The system of the present disclosure may be configured to guide a needle to a range of structures, for instance, a tissue, vessel, tumor, organ, lesion, area of skin, lumen, or body cavity. Thus, in some embodiments, block 501 could include orienting and/or adjusting the transducers so that the desired target location is within the viewing planes (i.e., image region) of the transducers of the probe. In some cases, the system could be configured for external use, and positioning the first transducer and the second transducer could include positioning the first transducer and the second transducer over a skin area of the subject. In such examples, the transducers may be placed such that a needle inserted through the needle guide is configured to extend in a direction substantially perpendicular to the skin of the subject.

Additionally or alternatively, in some embodiments the system could be configured for internal use (e.g., use within a body cavity, for instance, the gastrointestinal tract, bronchial tree, rectum, vagina, urethra, ureter, biliary tree, peritoneal cavity, or pleural cavity). As described elsewhere herein, such embodiments could be incorporated into an endoscopic probe, an endocavity probe, an endocavitary probe, or other types of internal diagnostic or interventional devices without limitation. In such scenarios, the transducers could be arranged within a probe configured for internal use. Positioning the first transducer and the second transducer could include inserting the probe into a body cavity of the subject or inserting the probe into a lumen of the subject. Other target locations and methods of positioning are contemplated.

In some cases, method 500 could also include adjusting the system such that the target location is within the viewing planes of the transducers. For example, various aspects of the system could be adjusted to guide a needle to a feature deep (e.g., more than 5 mm in depth from a skin surface) within a subject (e.g., an organ or blood vessel) or, alternatively, to a superficial feature (e.g., a portion of skin or a subcutaneous structure). Various aspects of the transducers could be adjusted before or during use in order to optimally guide a needle while visualizing the needle throughout its path from the needle guide to the target location. In a particular example, the transducers could be adjusted so as to select a propagation direction of sound waves emitted by the first transducer and the second transducer such that the sound waves are controllably emitted toward the target location. Additionally or alternatively, adjusting the first and/or second transducers could include adjusting the frequency of the sound waves emitted from the transducers. Such aspects of the transducer operations may be adjusted using a controller communicatively coupled to the first and/or second transducers, or based on interactions with a user interface of the system.

Block 502 of method 500 includes causing the first transducer and the second transducer to emit sound waves, such that at least a portion of the sound waves are emitted toward the target location. As described in relation to FIGS. 1A, 1B, 2A, 2B, 3, and 4, the transducers could be configured in a variety of shapes, arrangements, directions, and beam shapes. Causing the first transducer and the second transducer to emit sound waves could include causing the transducers to provide sound waves that propagate in the direction of the target location, such that the target location is within a viewing plane of the transducers. In some embodiments, sound waves emitted by the transducers include a frequency within a frequency range of about 1 MHz to 20 MHz. However, other frequencies and frequency ranges are contemplated.

Block 503 of method 500 includes receiving, at the first and second transducer, information indicative of reflected sound waves. The information indicative of reflected sound waves could include information relating to a timing of the sound waves, a magnitude of the sound waves, or the spatial location of an incident sound wave. As such, the collected information may be used to determine a location of the needle of another feature in the viewing plane, a depth or distance of the needle or feature, or some other information about the target location.

Block 504 of method 500 includes generating a real-time image of the target location based on the received information. In some examples, a controller of the device is configured to process the information (i.e., the raw data) received from the first and second transducers prior to constructing an image of the target location. For instance, data processing could include analog signal conditioning to adjust the temporal shape of the received information at individual transducer elements; combining the signals from each transducer element into a single signal representing different spatial locations, and/or adjusting the temporal shape of the combined ultrasound data. Additional data processing could include filtering and noise reduction steps.

A controller, such as controllers 190, 290, or 390 as illustrated and described in reference to FIGS. 1A, 2A, and 3, may further be configured to merge the information received from the transducers in real-time to create a multilayered and/or 3-dimensional image. In some examples, the controller could be an ultrasound image processing unit. Additionally or alternatively, the controller could include software configured to render a real-time 3-dimensional image based on a plurality of images of the needle and/or target location. In reference to FIG. 6A, method 500 could include producing multiple images (e.g, ultrasound images) corresponding to respective views of the target location from each of the plurality of transducers. In such an example, a first image 602 of the target location is produced based on the reflected sound waves received at the first transducer, and a second image 604 of the target location is produced based on the reflected sound waves received from the second transducer. As shown in FIG. 6B, a real-time image 606 of the target location may then be formed by overlaying the two or more images 602, 604 generated by the first and second transducers. In such a scenario, generating a real-time image 606 of the target location based on the received information could include generating a first image 602 of the target location based on information received by the first transducer; generating a second image 604 of the target location based on information received by the second transducer; and overlaying the first image 602 and the second image 604 to provide the real-time image 606.

Figure 6A:
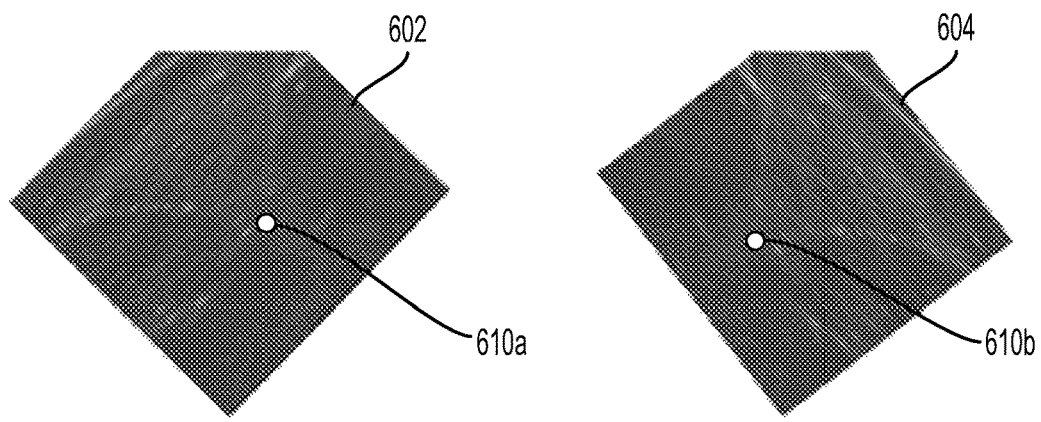
FIG. 6A shows ultrasound images of a target location generated according to an example embodiment.
Figure 6B:
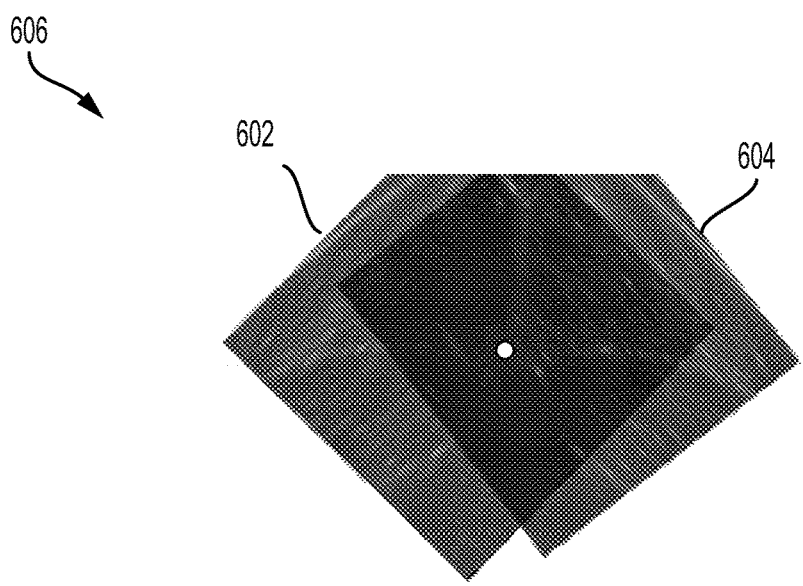
FIG. 6B shows the ultrasound images of FIG. 6A overlaid to provide a real-time image of an image region, according to an example embodiment.

As illustrated in FIGS. 6A-B, a plurality of images 602, 604 from a plurality of respective transducers may be merged to generate a real-time image of the target location. In some examples, the real-time image could be a 3-dimensional image generated (i.e., rendered) based on images from a first transducer, a second transducer, and/or further transducers. The 3-dimensional real-time image may be generated by determining a spatial location of the plurality of transducers, and using their relative spatial arrangement to render a 3-dimensional image. In one example, overlaying the first image 602 and the second image 604 could include determining a relative angle between a plane of the first transducer and a plane of the second transducer. A real-time 3-dimensional rendering could be generated based on at least the relative angle between the planes of the first and second transducers. Additional information relating to the transducers could also be used to generate a 3-dimensional real-time image. For instance, in some examples the information could include a distance between the first transducer and the second transducer, a distance and/or angle between the first and/or second transducer and the target location, or some other information.

Images from the two or more transducers could be overlaid based on identifying a structure (e.g., a structure representing the location of the needle or another feature in the target location) that is visible in both the first image 602 and the second image 604. For example, in the ultrasound images shown in FIGS. 6A-B, the location of the tip of the needle 610a, 610b is indicated with a white dot. A plurality of images displaying the same feature (e.g., a tip of a needle 610a, 610b) may be superimposed by identifying the location of the needle or other shared features in each image 602, 604, and overlaying the images so that the shared features converge (e.g., by overlapping the location of the needle in the first image 610a with the location of the needle in the second image 610b). In such a scenario, overlaying the first image 602 and the second image 604 could include determining a first structure 610a corresponding to the needle in the first image 602 and determining a second structure 610b corresponding to the needle in the second image 604. Overlaying the images 602, 604 could then include overlaying the first image 602 and the second image 604 based on a superimposition of the first structure 610a and the second structure 610b. Additionally or alternatively, other features of the target location could be used to overlay the images 602, 604. In various examples, these features could include vessels, organs, lumens, tissue interfaces, tumors, lesions, or other biological structures visible in the two or more ultrasound images.

As described in relation to FIGS. 3 and 4, in certain examples the probe could include a third or further transducer, and a real-time image could be generated with information received from the plurality of transducers. The method 500 may then include positioning a third transducer proximate to the target location; causing the third transducer to emit sound waves, such that at least a portion of the sound waves emitted from the third transducer are emitted toward the target location; and receiving, at the third transducer, information indicative of reflected sound waves. After receiving information indicative of reflected sound waves at the third transducer, this additional information may then be used for rendering a real-time image, i.e., information from the third transducer may be used to generate a third image of the target location, and the third image may be overlaid on the first and/or second images to generate a real-time image.

Furthermore, block 505 of method 500 includes inserting a needle through the needle guide so as to intersect with the target location. The path of the needle through the guide and into the subject may pass through overlapping viewing planes provided by the first and second transducer, such that the needle is visualized in the real-time image. In other words, in some embodiments herein the needle guide constrains the needle in a specified path, the path extending toward the target location. Inserting the needle through the needle guide could include extending the needle along the specified path. In some examples, the specified path extends perpendicular to the subject's skin, and inserting the needle through the needle guide could comprise inserting the needle substantially perpendicular to a skin surface of the subject. However, in other examples, the specified path could be oriented at any angle relative to skin of a subject, relative to the probe, or on another specified path. In yet further examples, the needle and/or needle guide may be manipulable, such that a user of the method can control the path of the needle. A user of method 500 may then be able to manipulate the needle as necessary to reach the target location or a feature within the target location.

The example method 500 illustrated in FIG. 5 is meant as an illustrative, non-limiting example. Blocks and steps described herein may be carried out sequentially or in parallel. Furthermore, the various block and steps could be carried out in a different order than described herein and some blocks and steps could be omitted, skipped, and/or repeated. Additional or alternative elements of the method and additional or alternative components of the system are contemplated.

What is claimed is:

1. A system comprising:
a probe comprising:
a first transducer configured to provide sound waves propagating along a first propagation direction; and
a second transducer configured to provide sound waves propagating along a second propagation direction, wherein the first transducer and the second transducer are arranged at an angle such that sound waves provided by the first and second transducers create an overlapping viewing plane over a target location of a subject; and
a needle guide detachably coupled to the probe, wherein the needle guide is disposed between the first transducer and the second transducer such that a needle inserted through the needle guide is configured to extend toward the target location and intersect the overlapping viewing plane.

2. The system of claim 1, wherein at least one of the first transducer or the second transducer comprise a linear array transducer.

3. The system of claim 1, wherein the first transducer and the second transducer are surrounded by a housing of the probe.

4. The system of claim 3, wherein the first transducer and the second transducer are arranged in a concave shape within the housing.

5. The system of claim 3, wherein the first transducer and the second transducer are permanently affixed to the housing.

6. The system of claim 1, wherein the probe further comprises a third transducer, wherein the third transducer is arranged such that sound waves provided by the third transducer are emitted toward the target location.

7. The system of claim 6, wherein the first transducer comprises a first transducer pair, wherein the second transducer comprises a second transducer pair, wherein the third transducer comprises a third transducer pair, and wherein the first transducer pair, the second transducer pair, and the third transducer pair are arranged in parallel such that each respective transducer pair is a fixed distance away from an adjacent transducer pair.

8. The system of claim 6, wherein the first transducer, the second transducer, and the third transducer are coupled according to an arrangement, wherein the arrangement comprises a concave shape.

9. The system of claim 6, wherein the first transducer, the second transducer, and the third transducer are arranged about a central axis, and wherein the needle guide is configured such that a needle inserted into the needle guide extends along the central axis toward the target location.

10. The system of claim 1, further comprising a controller communicatively coupled to the first transducer and the second transducer.

11. The system of claim 10, wherein the controller communicates with the first and second transducers via a wireless communication protocol.

12. The system of claim 10, wherein the controller is configured to adjust a frequency of sound waves emitted by at least one of: the first transducer or the second transducer.

13. The system of claim 1, wherein the needle guide comprises a coupler configured to secure the needle guide to the probe, wherein the coupler comprises at least one of: a shaft coupling, a magnetic coupling, a clip coupling, or a mating coupling.

14. The system of claim 1, wherein the sound waves comprise one or more frequencies within a frequency range of about 1 MHz to 22 MHz.

* * * * *